US00RE38435E

(19) United States
(12) Reissued Patent
Okamoto et al.

(10) Patent Number: US RE38,435 E
(45) Date of Reissued Patent: Feb. 24, 2004

(54) SEPARATING AGENT

(75) Inventors: Yoshio Okamoto, Amagasaki (JP); Koichi Hatada, Ikeda (JP); Tohru Shibata, Himeji (JP); Ichiro Okamoto, Himeji (JP); Hiroyuki Nakamura, Himeji (JP)

(73) Assignee: Daicel Chemical Industries, Ltd., Tokyo (JP)

(21) Appl. No.: 08/934,791

(22) Filed: Sep. 22, 1997

Related U.S. Patent Documents

Reissue of:
(64) Patent No.: 4,818,394
Issued: Apr. 4, 1989
Appl. No.: 07/144,628
Filed: Jan. 11, 1988

U.S. Applications:
(63) Continuation of application No. 08/509,947, filed on Aug. 1, 1995, now abandoned, which is a continuation of application No. 08/087,200, filed on Jul. 2, 1993, now abandoned, which is a continuation of application No. 07/635,954, filed on Dec. 28, 1990, now abandoned, which is a continuation of application No. 06/684,565, filed on Dec. 21, 1984, now abandoned.

(30) Foreign Application Priority Data

Dec. 28, 1983 (JP) ..... 58-245667

(51) Int. Cl.[7] ..... B01D 15/08
(52) U.S. Cl. ..... 210/198.2; 210/502.1; 210/635; 210/656; 502/404; 536/63; 536/64
(58) Field of Search ..... 536/63, 64; 502/150, 502/401, 404; 210/635, 656, 657, 658, 659, 198.2, 198.3, 502.1

(56) References Cited

U.S. PATENT DOCUMENTS 3,416,993 A * 12/1968 Heusser ..... 502/404
3,562,289 A * 2/1971 Battista ..... 210/656
3,570,673 A * 3/1971 Dutz ..... 210/198.2
3,597,350 A * 8/1971 Determann ..... 210/656
3,664,967 A * 5/1972 Stehl ..... 210/635
3,808,125 A * 4/1974 Good ..... 210/198.2
3,869,409 A * 3/1975 Bebris ..... 210/635
3,878,092 A * 4/1975 Fuller ..... 210/198.2
3,892,678 A * 7/1975 Halasz ..... 502/401
3,947,352 A * 3/1976 Cuatrecasas ..... 502/404
3,950,282 A * 4/1976 Gilbert ..... 424/78
3,960,720 A * 6/1976 Porath ..... 210/198.2
3,975,293 A * 8/1976 LePage ..... 210/635
4,111,838 A * 9/1978 Schaeffer ..... 210/656
4,272,503 A * 6/1981 Camin ..... 422/61
4,293,415 A * 10/1981 Bente ..... 210/198.2
4,303,529 A * 12/1981 Huckins ..... 210/635
4,322,310 A * 3/1982 House ..... 210/635
4,324,681 A * 4/1982 House ..... 210/659
4,330,440 A * 5/1982 Ayers ..... 210/635
4,335,017 A * 6/1982 Miles ..... 210/635

(List continued on next page.)

FOREIGN PATENT DOCUMENTS

EP 64833 * 11/1982 ..... 210/635

OTHER PUBLICATIONS

Mikes Laboratory Handbook of Chromatographic and Allied Methods, John Wiley and Sons, New York, 1979, p. 479, 480, 540, and 541.*

(List continued on next page.)

*Primary Examiner*—Ernest G. Therkorn
(74) *Attorney, Agent, or Firm*—Flynn, Thiel, Boutell & Tanis, P.C.

(57) ABSTRACT

A mixture of chemical substances such as optical isomers, geometrical isomers and polymers having different molecular weight ranges is separated to each ingredient by use of a cellulose derivative having an aromatic ring in the chromatographic method.

8 Claims, 1 Drawing Sheet

U.S. PATENT DOCUMENTS

| | | | | | |
|---|---|---|---|---|---|
| 4,336,161 | A | * | 6/1982 | Rosevear | 210/635 |
| 4,375,495 | A | * | 3/1983 | Yuki | 428/402 |
| 4,431,544 | A | * | 2/1984 | Atkinson | 210/635 |
| 4,431,546 | A | * | 2/1984 | Hughes | 210/656 |
| 4,443,366 | A | * | 4/1984 | Sakagami | 210/635 |
| 4,451,374 | A | * | 5/1984 | Peterson | 210/198.2 |
| 4,509,964 | A | * | 4/1985 | Hubball | 210/198.2 |
| 4,512,896 | A | * | 4/1985 | Gershoni | 210/635 |
| 4,517,241 | A | * | 5/1985 | Alpert | 210/635 |
| 4,529,521 | A | * | 7/1985 | Cortes | 210/635 |
| 4,544,485 | A | * | 10/1985 | Pinkerton | 210/635 |
| 4,549,965 | A | * | 10/1985 | Davis | 210/635 |
| 4,565,832 | A | * | 1/1986 | Kobashi | 210/635 |

OTHER PUBLICATIONS

Hesse, Die Chromatographische Racemattrennung , Lie bigs Ann. Chem. 1976, p. 996–1000.*

Hagel, Chromatographische Racemattrennung An Cellulosetriacetat, 1976, pp. 134 and 135.*

Optical Resolution on Polymers by Yoshio Okamoto—A publication presented at the 49th Spring Meeting of the Chemical Society of Japan Mar. 10, 1984 (entire document).*

1983 International Symposium on Wood and Pulping Chemistry, vol. 1, "Preparation of Cellulose Derivatives by the Use of Non–Aqueous Cellulose Solvents", by J. Nakano et al., pp. 70–75.*

"Dai–Yuki Kagaku" 19, Tennen Kobunshi Kagaku I published by Asakura Book Store, pp. 124 and 93. Husemann et al., "Makromol. Chem", 176, 3269 (1975).*

N. M. Bikales, L. Segel, "Cellulose and Cellulose Derivatives", pp. 807–809.

1983 International Symposium on Wood and Pulping Chemistry, vol. 1, "Preparation of Cellulose Derivatives by the Use of Non–Aqueous Cellulose Solvents", by J. Nakano et al, pp. 70–75.

* cited by examiner

SEPARATING AGENT

Matter enclosed in heavy brackets [ ] appears in the original patent but forms no part of this reissue specification; matter printed in italics indicates the additions made by reissue.

[This application is a continuation of U.S. Ser. No. 684,565, filed Dec. 21, 1984, now abandoned.] *This application is a reissue continuation of U.S. Ser. No. 08/509,947, filed Aug. 1, 1995, now abandoned, which is a reissue continuation of U.S. Ser. No. 08/087,200, filed Jul. 2, 1993, now abandoned, which is a reissue divisional of reissue application Ser. No. 07/982,029, filed Nov. 24, 1992, now U.S. Reissue Pat. No. 34,457, issued on Nov. 30, 1993, which is a reissue continuation application of reissue application Ser. No. 07/635,954, filed Dec. 28, 1990, now abandoned, which is a reissue application of Ser. No. 07/144,628 filed Jan. 11, 1998, now U.S. Pat. No. 4,818,394, issued on Apr. 4, 1989, which is a continuation of application Ser. No. 06/684,565, filed Dec. 21, 1984, now abandoned.*

The invention relates to use of a cellulose derivative having a group containing an aromatic group as a separating agent for a chemical substance. The invention method applies to separation of optical isomers, geometrical isomers and polymers having different molecular weight ranges from each other. They have not easily been separated in the state of prior arts.

Generally, the physiological activity of a racemic compound often differs from that of an optically active compound. For example, in the field of medicines, pesticides or the like, it is sometimes necessary to resolve optical isomers for the purposes of preventing adverse reactions and improving the medicinal effects per unit dose. A mixture of optical isomers has been divided by a preferential crystallization process or diastereomer process. However, variaties of the compound which can be optically resolved by these processes are limited and most of these processes require a long time. Under these circumstances, development of a convenient chromatographic resolution process has eagerly been demanded.

The chromatographic resolution of optical isomers has been investigated from old times. For instance, cellulose and a triacetate thereof have been successfully used as column-chromatographic resolving agents in optical resolution. The cellulose and cellulose triacetate are those belonging to cellulose I and cellulose triacetate I, respectively. However, substances which can be resolved by said cellulose or a derivative thereof are limited and the resolving ability of them is insufficient.

After intensive investigations, the inventors have found surprisingly that a cellulose derivative having a group containing an aromatic ring has excellent ability in separation of chemical substances and isomers, in particular optical isomers. The invention has been completed on the basis of the finding.

The invention relates to a method for separating a chemical substance from a mixture containing the same, which comprises the step of treating said mixture with a cellulose derivative having a group containing an aromatic ring, a separating agent comprising the cellulose derivative; particles of the separating agent; a packing material of the particles; and a chromatographic column filled with the agent.

Though the reasons why the cellulose derivatives having an aromatic ring used in the present invention have excellent effects for resolving the optical isomers have not been elucidated yet, it may be considered that the ordered asymmetic structure of cellulose and the aromaticity and rigidity of the aromatic group exert a great influence on the resolution of the optical isomers.

The cellulose derivative according to the invention is preferred to have a number-average degree of polymerization of 5 to 5000, preferably 10 to 1000, and particularly 10 to 500. The average degree of substitution of the cellulose derivative having an aromatic ring is defined by the following formula:

$$\text{Average degree of substitution} = \frac{\text{Number of substituents in the molecule}}{\text{Number-average degree of polymerization}}$$

The average degree of substitution of the cellulose derivatives having an aromatic ring of the present invention is 1 to 3.4, preferably 1.8 to 3.2.

The unreacted hydroxyl groups in the aromatic cellulose derivative containing aromatic rings may further be esterified, carbamoylated or etherified so far as its capacity of resolving optical isomers is not damaged.

The cellulose derivative of the invention may include those in which part or all of the hydrogen atoms of the hydroxyl groups have been replaced with an aromatic group or a group containing an aromatic group. A substituent may be attached to cellulose by way of an intermediate linkage such as an ester, an ether and an urethane. The term "aromatic group" includes that derived from an aromatic ring having 6 to 20 carbon atoms, an aralkyl group having 6 to 20 carbon atoms in the aryl portion and 1 to 4 carbon atoms in the alkyl portion and a heteroaromatic ring having 3 to 20 carbon atoms. The ring may further have a substituent thereon, such as an alkyl group, nitro group, a halogen, an amino group, an alkyl-substituted amino group, cyano group, hydroxyl group and carboxyl group.

Now, the description will be made on processes for the production of the substances of the present invention. The cellulose derivatives substituted through an ester group include, cellulose benzoate for example. The esterification reaction to obtain them may be carried out by a known process, (See "Dai-Yuki Kagaku" 19, "Tennen Kobunshi Kagaku" I published by Asakura Book Store, p. 124). Examples of the esterifying agents include benzoyl derivatives having the following structures such as benzoyl chloride:

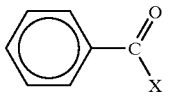

(X: leaving group)

The reaction solvent may be any solvent such as pyridine and quinoline, so far as it does not inhibit the esterification reaction. Frequently a catalyst such as 4-(N,N-dimethylamino)pyridine is effective in accelerating the reaction. Other aromatic derivatives may be obtained by the esterification reaction in the same manner as described above.

The cellulose derivative substituted through an ether group may be obtained by a known process for etherifying cellulose. Generally, they are obtained by reacting cellulose with an aromatic derivative having a leaving group in the presence of a base. This process has been disclosed in, for example, N. M. Bikales, L. Segel, "Cellulose and Cellulose Derivatives" p. 807 and "Dai-Yuki Kagaku" 19 published by Asakura Book Store, p. 93. Processes for producing cellulose ethers having an aromatic ring of a high degree of substitution includes that of Husemann et al. ("Makromol. Chem,", 176, 3269 (1975)) and that of Nakano et al. ("The Processings of ISWPC" #1983, Vol. 1, 33).

The cellulose derivatives substituted through an urethane group may be produced by a conventional process wherein an isocyanate is reacted with an alcohol to form a urethane.

For example, these compounds may be produced by reacting an isocyanate having an aromatic ring with cellulose in the presence of a Lewis base catalyst such as a tertiary amine base or a Lewis acid catalyst such as a tin compound.

The disubstituted urethanes may be synthesized in the same manner as in the above-mentioned esterification reaction using a disubstituted carbamoyl halide or the like.

In using the resolving agent of the present invention containing the cellulose derivatives having an aromatic ring as the principal component for the purpose of resolution, it is preferred to employ a chromatographic method. The preferred chromatographic methods include liquid, thin layer and gas chromatography.

In using the separating agent of the present invention in the liquid or gas chromatography, there may be employed a method wherein the aromatic ring-containing cellulose derivative is packed into a column directly or in the form supported on a carrier or a method wherein a capillary column is coated with said cellulose derivative.

Since the chromatographic separating agent is preferably in the form of granules, the aromatic ring-containing cellulose derivative to be used as the resolving agent is preferably ground or shaped into beads. The particle size which varies depending on the size of a column or plate used is generally 1 $\mu$m to 10 mm, preferably 1 to 300 $\mu$m. The particles are preferably porous.

It is preferred to support the aromatic ring-containing cellulose derivative on a carrier so as to improve the resistance thereof to pressure, to prevent swelling or shrinkage thereof due to solvent exchange or to reduce the number of theoretical plates. The suitable size of the carrier which varies depending on the size of the column or plate used is generally 1 $\mu$m to 10 mm, preferably 1 to 300 $\mu$m. The carrier is preferably porous and has an average pore diameter of 10 Å to 100 $\mu$m, preferably 50 to 50,000 Å. The amount of said cellulose derivative to be supported is 1 to 100 wt. %, preferably 5 to 50 wt. %, based on the carrier. The carrier is preferred to have a ratio of the pore size to the particle size in the range of not larger than 0.1.

The aromatic ring-containing cellulose derivative may be supported on the carrier by either chemical or physical means. For example, the cellulose derivative is dissolved in a suitable solvent, then the solution is mixed uniformly with a carrier and the solvent is distilled off under a reduced pressure or by heating. Alternatively, the cellulose derivative is dissolved in a suitable solvent, the resulting solution is mixed homogeneously with a carrier and the mixture is dispersed in a liquid incompatible with said solvent by stirring to diffuse the solvent. The cellulose derivative thus supported on the carrier may be crystallized, if necessary, by heat treatment or the like. Further, the state of the supported cellulose derivative and accordingly its resolving power can be modified by adding a small amount of a solvent thereto to temporarily swell or dissolve it and then distilling the solvent off.

Both porous organic and inorganic carriers may be used, though the latter is preferred. The suitable porous organic carriers are those comprising a high molecular substance such as polystyrene, polyacrylamide or polyacrylate. The suitable porous inorganic carriers are synthetic or natural products such as silica, alumina, magnesia, titanium oxide, glass, silicate or kaolin. They may be treated on the surface so as to improve the affinity with the separating agent of the invention. The surface-treatment may be conducted with use of an organosilane compound or by plasma polymerization.

In using the cellulose derivatives in the optical resolution, the resolving characteristics thereof may vary sometimes depending on the physical states thereof such as molecular weight, crystallinity and orientation, even though they are chemically similar. Therefore, the cellulose derivatives may be subjected to a physical or chemical treatment such as heat treatment or etching in the course of or after shaping them suitable for use.

As to the developers for the liquid chromatography, solvents in which the aromatic ring-containing cellulose derivative is soluble cannot be used. However, the developers are not particularly limited when the aromatic ring-containing cellulose derivative is chemically bound to the carrier or when it is cross-linked.

In the thin layer chromatography, a layer having a thickness of 0.1 to 100 mm and comprising the resolving agent in the form of particles of about 0.1 $\mu$m to 0.1 mm and a small amount of a binder is formed on a supporting plate.

The aromatic ring-containing cellulose derivative may be spun into a hollow fiber in which an eluent containing the compound to be resolved is to flow so that the resolution is effected by virtue of the adsorption of the compound on the inner wall of the filament. In another embodiment, the cellulose derivative is spun into an ordinary filament, which is then bundled in parallel and placed in a column so as to take advantage of the adsorption on the surface thereof. In the membrane resolution process, the resolving agent may be used in the form of a hollow fiber or film.

The resolving agent of the present invention comprising the aromatic ring-containing cellulose derivative as a principal constituent is effective for the resolution of compounds. Particularly, it is quite effective for the resolution of optical isomers which are quite difficult to resolve in the prior art. This way the optical isomer mixture to be treated in the invention includes a compound having the asymmetric center and one having the molecular asymmetry such that either one of the optical isomers may be preferably adsorbed on the separating agent of the invention.

We explain the term, "heteroaromatic derivative" of the invention. It preferably includes an ester between a cellulose and a carboxylic or carbamic acid having a heteroaromatic group or a substituted heteroaromatic group. The heteroaromatic group has 3 to 20 carbon atoms. Among them, an acyl group, a carbamoyl group and alkyl group are more preferable. Especially an acyl and carbamoyl are best. Embodiments are illustrated below.

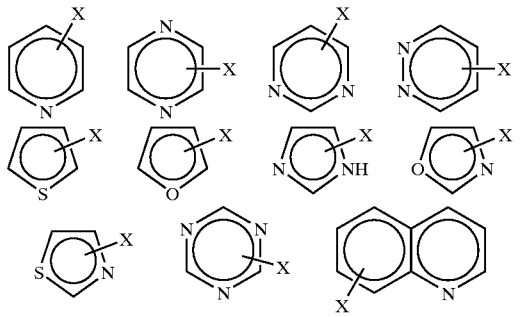

-continued

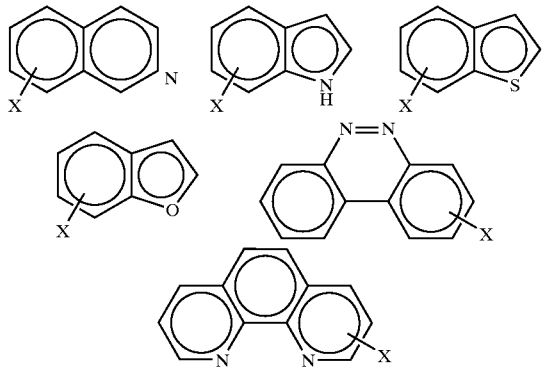

wherein X represents

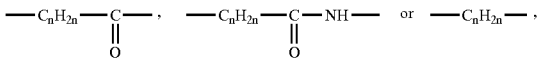

n being an integer of 0 to 5, preferably 0 or 1.

The term "substituted aromatic ester" herein involves a carboxylic acid ester having an aromatic group wherein one or more hydrogen atom(s) is (are) replaced with one or more atom(s) or atomic group(s). The alcoholic moiety of the ester comprises the above-mentioned polysaccharide. The carboxylic acids have preferably acyl groups of the following formula:

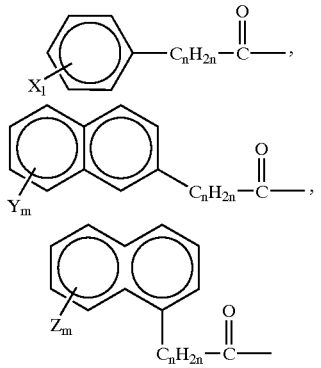

wherein X, Y and Z each represents an alkyl group, alkenyl group, alkynyl group, nitro group, halogen atom, amino group, alkyl-substituted amino group, cyano group, hydroxyl group, alkoxy group, acyl group, thiol group, sulfonyl group, carboxyl group or alkoxycarbonyl group, l and m represent the numbers of X, Y and Z groups (l being an integer of 1 to 5, m being an integer of 1 to 7 and n being an integer of 0 to 5, preferably 0).

30 to 100%, preferably 85 to 100%, on average of the hydroxyl groups of the polysaccharide moiety in the aromatic ester should be esterified with the carboxylic acid.

The balance of the hydroxyl groups may be present in the form of free hydroxyl groups or they may be esterified, etherified or carbamoylated so far as the resolving capacity of the resolving agent is not damaged.

Now, the description will be made on the process for the esterification to form a cellulose derivative to be used in the present invention. A substituted benzoic ester may be produced by a known process (See, for example, "Dai-Yuki Kagaku" 19, 'Tennen Kobunshi Kagaku I' published by Asakura Book Store, p. 124). Examples of the esterifying agents include benzoyl derivatives of the following formula, particularly, benzoyl chloride:

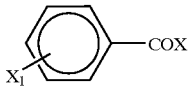

(X: leaving group)

Any solvent may be used in the reaction so far as it does not inhibit the esterification. Pyridine and quinoline are preferred. Frequently, a catalyst such as 4-(N,N-dimethylamino)pyridine is effective in accelerating the reaction.

The esters may also be obtained by reacting the corresponding carboxylic anhydride or a combination of the carboxylic acid with a suitable dehydrating agent with the polysaccharide.

Other ester derivatives of the present invention may be synthesized according to the above-mentioned process for the synthesis of the substituted benzoic esters.

The resolving agent of the present invention containing the substituted aromatic ester as the effective component is effective for the resolution of various compounds. Particularly, it is quite effective for the resolution of optical isomers which are quite difficult to resolve. Either one of the optical isomers to be resolved is selectively adsorbed on the resolving agent.

Particularly, according to the present invention, the resolving and adsorbing properties of a resolving agent are varied by introducing a substituent therein to improve the intended resolving effects, particularly, optical resolving effects. For example, the effects of cellulose tribenzoate will be compared with those of a chlorine-substitured derivative thereof. A Tröger's base which can not be optically resolved by the tribenzoate can be resolved by tris-4-chlorobenzoate with an α-value of 1.25. Benzoin which is resolved by the tribenzoate with an α-value of 1.14 exhibits an α-value of 1.26 in the resolution by the tris-3-chlorobenzoate. Similarly, benzoin, 2-phenylcyclohexanone and mandelamide are optically resolved with the tris-3,5-dichlorobenzoate far more easily than with the tribenzoate. Though the relationship between the remarkable change in resolving characteristics and the substitution has not fully been elucidated, the change might be caused by a complicated combination of factors such as influence of a substituent on the shape of the molecule, physico-chemical properties, such as polarizability, hydrogen bonding ability and polarity, of the substituent and electronic effects of the substituent on the π-electron system of the aromatic ring.

It is thus apparent from the present invention that the substituent has a quite effective influence on the modification of the resolving characteristics of the resolving agent and the development of resolving agents having various characteristics has been made possible. These effects are expected also in various other resolving agents have polysaccharides other than cellulose as the skeleton.

Particularly, by modifying the polysaccharides with the substituent having a sufficient length, the asymmetrical structure of the polysaccharide is further developed to obtain a higher capacity of resolving the optical isomers.

The above-mentioned objects of the present invention can be attained with the resolving agent containing an aralkylcarboxylic ester of a polysaccharide as the effective component.

The resolving agent of the present invention exhibits preferably different absorbing capacities on respective optical isomers of a compound.

The term "aralkylcarboxylic acids" herein involves substitution derivatives of acetic acid and they include aliphatic carboxylic acids having an aromatic substituent in the molecule and various substitution derivatives of them, preferably arylacetic acid and aryloxyacetic acid derivatives. Acrylic acid derivatives, benzoic acid derivatives and propiolic acid derivatives must be excluded even if they contain an aromatic ring. The aromatic rings include, for example, phenyl, naphthyl, phenanthryl and anthryl rings. They may be bonded with the skeleton in any manner.

Examples of these compounds include the following compounds:

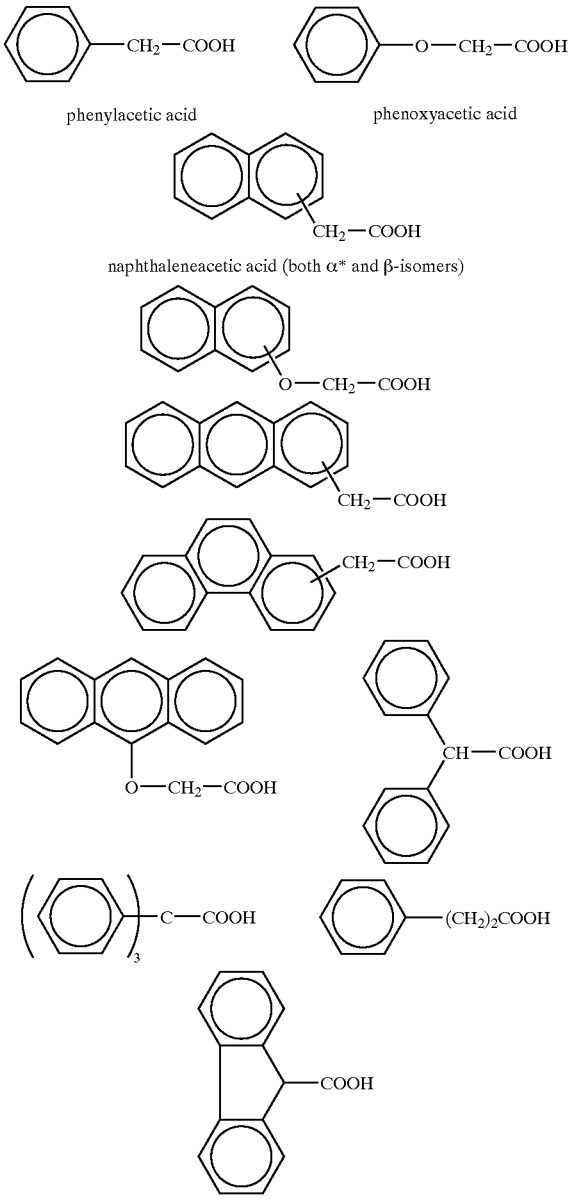

The aromatic ring may have various substituents so far as the effecs of the present invention are not damaged.

30 to 100%, preferably 85 to 100%, on average of the hydroxyl groups of the polysaccharides forming the polysaccharide/aralkylcarboxylic ester of the present invention should be esterified with the carboxylic acid. The balance of the hydroxyl groups may be present in the form of free hydroxyl groups of they may be esterified, etherified or carbamoylated so far as the resolving capacity of the resolving agent is not damaged.

The esterification for forming the compounds used in the present invention may be conducted by a known process for the esterification of cellulose or amylose (see, for example, "Dai-Yuki Kagaku" 19, 'Tennen Kobunshi Kagaku I' published by Asakura Book Store, p. 124, reference 1). Common esterifying agents are anhydrides and halides of the corresponding carboxylic acids, particularly acid chlorides.

It is preferred to use a tertiary amine base or a Lewis acid as a catalyst. Any reaction solvent may be used so far as it does not inhibit the reaction. For example, pyridine or quinoline which acts also as the base is used frequently. Further, a catalyst such as 4-(N,N-dimethylamino)pyridine is effective in accelerating the invention.

The corresponding carboxylic acid in combination with a suitable dehydrating agent may be reacted with the polysaccharide.

Since most of the polysaccharides used as the starting material have a low reactivity, it is preferred that they are activated by dissolution/reprecipitation or dissolution/freeze-drying treatment or by using a reaction solvent in which the polysaccharides are soluble.

Figure 1:
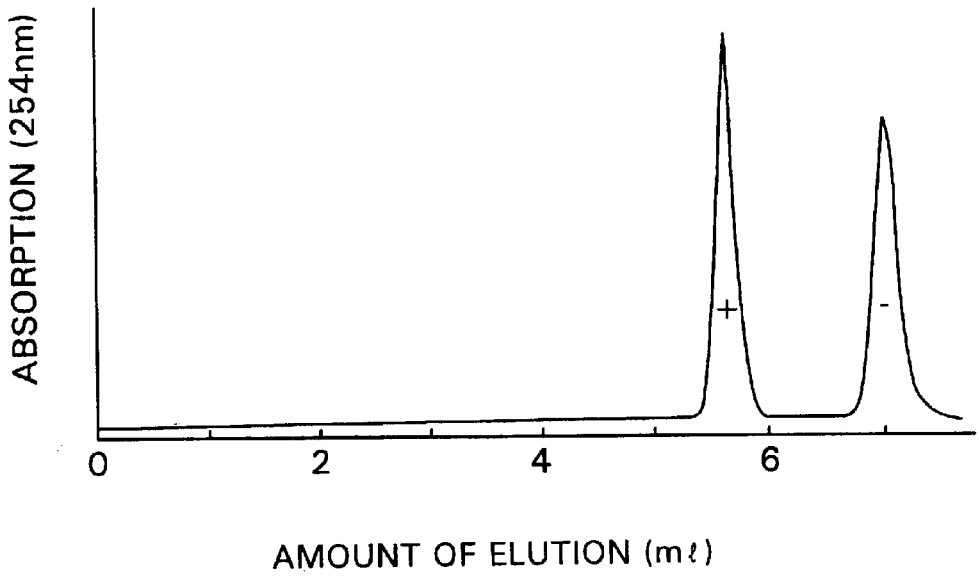
FIGS. 1 and 2 are charts showing the results of the optical resolution effected by using packings of the present invention for the optical resolution.

The invention will be illustrated below in reference to synthesis examples, examples and application examples. Each of the particular terms is defined below.

$$\text{volume ratio } (k') = \frac{[(\text{retention time of antipode}) - (\text{dead time})]}{(\text{dead time})}$$

$$\text{separation factor } (\alpha) = \frac{\left(\begin{array}{c}\text{volume ratio of antipode}\\ \text{adsorbed more strongly}\end{array}\right)}{\left(\begin{array}{c}\text{volume ratio of antipode}\\ \text{adsorbed less strongly}\end{array}\right)}$$

$$\text{rate of separation } (Rs) = \frac{\begin{array}{c}2\times(\text{distance between a pair of more}\\ \text{strongly adsorbed antipode and that}\\ \text{of less strongly adsorbed antipode})\end{array}}{(\text{total band width of both peaks})}$$

Synthesis Example 1

(Synthesis of Cellulose Benzoate)

① Synthesis of low-molecular weight cellulose triacetate:

100 g of cellulose triacetate having a number-average degree of polymerization of 110 and a degree of acetylation of 2.94 was dissolved in 100 ml of acetic acid. 5.2 ml of water and 5 ml of concentrated sulfuric acid were added to the solution and the mixture was maintained at 80° C. for 3 h to effect the reaction for obtaining a product of a lower molecular weight. After the completion of the reaction, the reaction mixture was cooled and sulfuric acid was neutralized with excess aqueous magnesium acetate solution. The solution was added to 3 l of water to precipitate cellulose triacetate of a low molecular weight. The precipitate was filtered through a G3 glass filter, dispersed in 1 l of water, further filtered and dried under vacuum. The obtained product was dissolved in methylene chloride and reprecipitated from 2-propanol. The dissolution and reprecipitation were repeated twice to purify the product, which was then dried.

From the IR and NMR spectra of the product, it was identified with cellulose triacetate. The number-average molecular weight of the product was 7900 (the degree of polymerization: 27) according to vapor pressure osmometry (Corona 117; chloroform/1% ethanol).

② Synthesis of cellulose having a low molecular weight:

5.0 g of the low-molecular weight cellulose triacetate prepared as above was dissolved in 50 ml of pyridine. 4.0 ml of 100% hydrazine hydrate was added to the solution. The mixture was left to stand at room temperature for 1 h and then heated to 90° to 100° C. A precipitate thus formed was filtered through a glass filter and washed with pyridine. The product containing pyridine was used in the subsequent reaction.

③ Synthesis of low-molecular weight cellulose tribenzoate:

The low-molecular weight cellulose obtained as above was dispersed in a mixture of 50 ml of pyridine and 21 ml of triethylamine. 200 mg of 4-(dimethylamino)pyridine as catalyst was added to the dispersion. 11.6 ml of benzoyl chloride was added dropwise slowly to the mixture under stirring. The resulting mixture was left to stand at room temperature for 3 h and then kept at 120° C. for 10 h to complete the reaction. The resulting pyridine solution was added to a large excess of methanol. A precipitate thus formed was filtered and washed with methanol. The product was dissolved in methylene chloride and reprecipitated from ethanol. This purification process was repeated three times.

From the IR and NMR spectra of the product, it was identified with cellulose tribenzoate. From the fact that no occurrence of acetylation was recognized in the NMR spectra after treating the product with acetic anhydride in pyridine, it may be concluded that the hydroxyl groups had been esterified into benzoate groups without leaving any free hydroxyl group intact.

Synthesis Example 2

(Synthesis of Packing for Use in the Optical Resolution)

① Treatment of silica gel with silane:

10 g of silica beads (Lichrospher SI 1000: a product of Merck & Co.) was placed in a 200 ml round-bottom flask with a side arm. After vacuum-drying in an oil bath at 120° C. for 3 h, the pressure was returned to atmospheric pressure, the temperature was lowered to room temperature and $N_2$ was introduced therein. 100 ml of toluene which had been preliminarily distilled was added to the dry silica beads. 3 ml of diphenyldimethoxysilane (KBM 202; a product of Shin'etsu Kagaku Co., Ltd.) was added to the mixture and they were stirred together and then reacted at 120° C. for 1 h. After distilling off 3 to 5 ml of toluene, the reaction was carried out at 120° C. for 2 h. The mixture was filtered under suction through a glass filter (G-4), washed with 50 ml of toluene three times and then with 50 ml of methanol three times and dried in vacuum at 40° C. for 1 h.

About 10 g of the silica beads treated as above were placed in the 200 ml round-bottom flask with a side arm. After vacuum drying at 100° C. for 3 h, the pressure was returned to the atmospheric pressure and the mixture was cooled to room temperature. Then, $N_2$ was introduced therein.

100 ml of distilled toluene was added to the dried silica beads. 1 ml of N,O-bis(trimethylsilyl)acetamide (a trimethylsilylating agent) was added thereto and the mixture was stirred to effect the reaction at 115° C. for 3 h.

The reaction mixture was filtered through a G-4 glass filter, washed with toluene and dried under vacuum for about 4 h.

② Coating 1.6 g of the cellulose benzoate obtained in Synthesis Example 1 was dissolved in 10.0 ml of methylene chloride and the solution was filtered through a G-3 glass filter.

3.5 g of the silica gel treated with silane was mixed with 7.5 ml of said cellulose benzoate solution and the solvent was distilled off under reduced pressure.

Example 1

The silica gel packing coated with cellulose benzoate obtained in Synthesis Example 2 was packed in a stainless steel column having an inner diameter of 0.46 cm and a length of 25 cm by a slurry method (solvent: methanol). Various racemic compounds were optically resolved according to high-performance liquid chromatography using this column to obtain the results shown in FIGS. 1 and 2 and Table 1.

The symbols (+ and −) in the figures and the table refer to the signs of optical rotation at 365 nm.

FIG. 1 is an optical resolution chart of trans-stilbene oxide

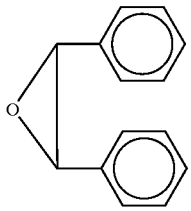

[flow rate: 0.2 ml/min; solvent: hexane/2-propanol (9:1)].

Figure 2:
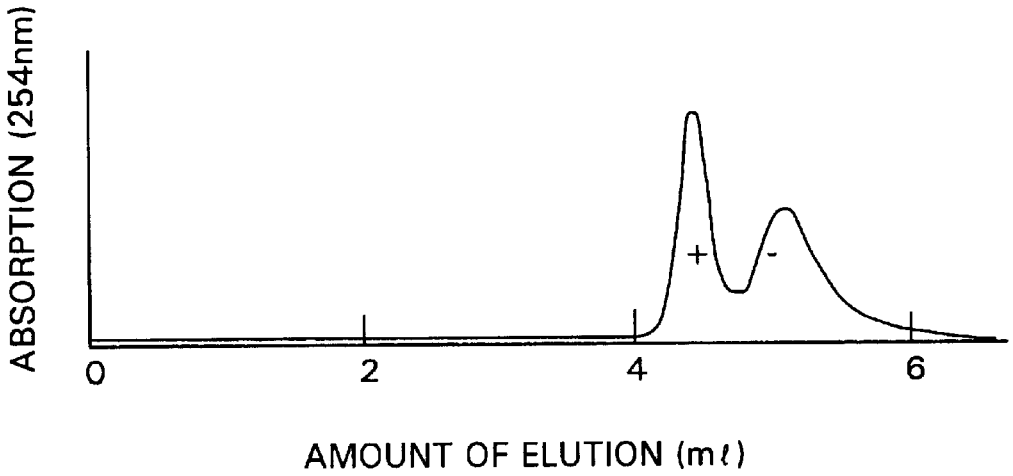

FIG. 2 is an optical resolution chart of a cyclobutane derivative:

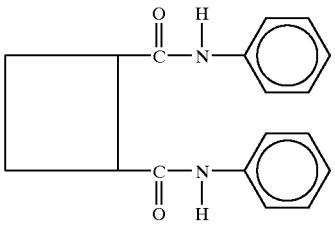

[flow rate: 0.2 ml/min, solvent; ethanol].

TABLE 1

Optical resolution of racemic compounds

| Racemic compounds | Volume ratio $k'_1$ | Volume ratio $k'_2$ | Separation factor α | Rate of separation (Rs) |
|---|---|---|---|---|
| trans-stilbene oxide 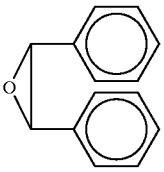 | 0.71 (+) | 1.00 (−) | 1.4 | 2.2 |
| 2-phenylcyclohexane 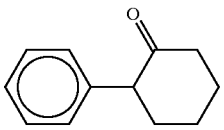 | 0.99 (−) | 1.14 (+) | 1.2 | 0.98 |
| cyclobutane derivative | 0.42 | 0.64 | 1.5 | 0.97 |

TABLE 1-continued

Optical resolution of racemic compounds

| Racemic compounds | Volume ratio $k'_1$ | Volume ratio $k'_2$ | Separation factor α | Rate of separation (Rs) |
|---|---|---|---|---|
| 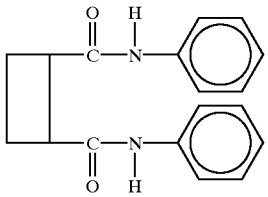 | (+) | (−) | | |
| benzoin 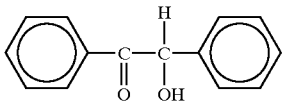 | 0.53 (+) | 0.58 (−) | 1.1 | — |

(Notes)
Column: 25 cm × 0.46 cm
Flow rate: 0.2 ml/min. solvent: ethanol.

Comparative Example 1

140 g of cellulose triacetate produced by an ordinary homogeneous acetylation process (number-average degree of polymerization as determined by vapor pressure osmometry: 110; molecular weight distribution $\overline{Mw}/\overline{Mn}$=2.45, free hydroxyl group content: 0.35%) was swollen in 1.4 l of acetic acid (a guaranteed reagent of Kanto Kagaku Co.). 23.2 ml of acetic anhydride, 7.0 ml of sulfuric acid and 8.4 ml of water were added thereto and the reaction was carried out at 80° C. for 3 h. The reaction mixture was cooled with ice/water and sulfuric acid was neutralized with 86.8 g of 26% aqueous magnesium acetate solution. A solution thus obtained was added to a solvent mixture of water/2-propanol to precipitate cellulose acetate which was then filtered and dried. The obtained cellulose acetate was dissolved in acetone. An insoluble matter was filtered out under pressure. Water was added to the residue in such an amount that no precipitate would be formed. The solvent was distilled off with a rotary evaporator. A white powder thus obtained was dried under reduced pressure.

From the results of X-ray diffractometry, it was found that the resulting crystalline cellulose acetate had a crystallinity of 46% and a half width of 0.58°. The average degree of polymerization determined based on the viscosity in a solvent mixture of methanol/methylene chloride (1:1) was 23. The free hydroxyl group content of the product was 0.8%. According to electron microscope observation, the product was in the form of porous particles having a diameter of 1 to 10μ. The resolution was effected in the same manner as in Example 1 except that the triacetylcellulose was packed by slurry process using methanol as the solvent. Trans-stilbene oxide had a resolution factor α of 1.34 and a rate of separation (Rs) of 0.91. No peak separation was observed with 2-phenylcyclohexanone and benzoin.

Synthesis Example 3

Cellulose triacetate having a number-average degree of polymerization of 110 and a degree acetylation of 2.94 was dissolved in 1 l of acetic acid. 5.2 ml of water and 5 ml of conc. sulfuric acid were added to the resulting solution and the reaction was carried out at 80° C. for 3 h. The reaction mixture was cooled and sulfuric acid was neutralized with an excess amount of an aqueous magnesium acetate solution. The resulting solution was added to 3 l of water to precipitate cellulose triacetate having a reduced molecular weight. After filtration through a glass filter (G3), it was dispersed in 1 l of water. After filtration followed by vacuum drying, the obtained product was dissolved in methylene chloride and reprecipitation from 2-propanol. The dissolution and the reprecipitation were repeated twice to effect the purification. The product was dried. According to the IR and NMR spectra, the product was identified as cellulose triacetate. The number-average molecular weight of the product as determined by vapor pressure osmometry was 7900, which corresponded to the number-average degree of polymerization of 27. The vapor pressure osmometry was conducted with a vapor pressure osmometer Corona 117 using a solvent mixture of chloroform/1% ethanol.

10.0 g of the resulting low-molecular weight cellulose triacetate was dissolved in 100 ml of pyridine. 8.0 ml of 100% hydrazine hydrate was added to the solution. The mixture was left to stand at room temperature for 1 h and then heated to 90° to 100° C. A precipitate thus formed was filtered through a glass filter and washed with pyridine. According to the IR spectrum, the resulting product was identified as cellulose.

Cellulose tribenzyl ether was synthesized from the resulting low-molecular weight cellulose by successive processes of Husemann et al. [Markromol. Chem., 176, 3269 (1975)]. The product was identified according to NMR and IR spectra. In the IR spectrum, no absorption due to the hydroxyl group was recognized at all. This fact suggested that the degree of substitution was about 3.

NMR ($CDCl_3$): δ7.1 (multiplets) 15H δ5.3~2.8 (multiplets) 13H.

IR (KBr disc.): 1950(w), 1870(w), 1805(w), 1740(w), 1605(m), 1500(m), 740(s), 700(s) all due to the substituted benzene ring. 1050~1100(vs) due to the glycoside bond

Synthesis Example 4

10 g of silica beads (LiChrospher SI 1000; a product of Merck & Co.) was placed in a 200 ml round-bottom flask with a side arm. After vacuum-drying in an oil bath at 120° C. for 3 h, $N_2$ was introduced therein. 100 ml of toluene which had been preliminarily distilled in the presence of $CaH_2$ was added to the silica beads. 3 ml of diphenyldimethoxysilane (KBM 202; a product of Shin'etsu Kagaku Co., Ltd.) was added to the mixture and they were stirred together and then reacted at 120° C. for 1 h. After distilling off 3 to 5 ml of toluene, the reaction was carried out at 120° C. for 2 h. The mixture was filtered through a glass filter, washed with 50 ml of toluene three times and then with 50 ml of methanol three times and dried in vacuum at 40° C. for 1 h.

About 10 g of the silica beads were placed in the 200 ml round-bottom flask with a side arm. After vacuum drying at 100° C. for 3 h, the pressure was returned to the atmospheric pressure and the mixture was cooled to room temperature. Then, $N_2$ was introduced therein. 100 ml of distilled toluene was added to the dried silica beads. 1 ml of N,O-bis (trimethylsilyl)acetamide (a trimethylsilylating agent) was added thereto and the mixture was stirred to effect the reaction at 115° C. for 3 h. The reaction mixture was filtered through a glass filter, washed with toluene and dried under vacuum for about 4 h.

Tribenzylcellulose obtained in Synthesis Example 3 was dissolved in chloroform. Methanol in an amount four times as much as chloroform was added to the solution to divide it into a soluble part and an insoluble part. 1.2 g of the soluble part was dissolved in a solvent mixture of methylene chloride and benzene (5 ml:2.5 ml). 6 ml of the resulting solution was mixed with 3.2 g of silane-treated silica gel. The solvent was distilled off under reduced pressure. The resulting silica beads were used as a packing for use in the optical resolution.

Example 2

The silica beads carrying tribenzylcellulose obtained in Synthesis Example 4 were packed in a stainless steel column having a length of 25 cm and an inner diameter of 0.46 cm by slurry process. The high-performance liquid chromatograph used was Trirotar-SR (a product of Nihon Bunko Kogyo Co., Ltd.) and the detector used was Uvidec-V. The flow rate was 0.2 ml/min and ethanol was used as the solvent. The results of resolution of various racemic compounds are shown in Table 2.

TABLE 2

Optical resolution of racemic modifications

| Racemic compound | Volume ratio $k'_1$ | Volume ratio $k'_2$ | Separation factor α | Rate of separation (Rs) |
|---|---|---|---|---|
| 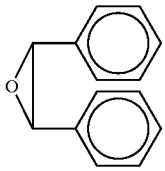 | 0.75 | 0.99 | 1.32 | 1.50 |
| 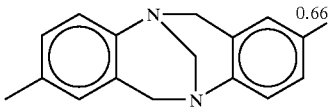 | 0.66 | 0.99 | 1.46 | 1.12 |

Synthesis Example 5

1 g of cellulose (cellulose for column chromatography; a product of Merck & Co.) was dispersed in 50 ml of dry pyridine. 8 ml of phenyl isocyanate was added to the dispersion and the mixture was kept stirred at 110° C. After 16 h, the reaction mixture was poured into 1 l of methanol. A white solid thus formed was filtered and dried at room temperature for 2 h and then at 60° C. for 3 h under reduced pressure. Yield: 1.45 g.

The product was substantially completely soluble in chloroform, methylene chloride and dioxane. The product was identified with cellulose trisphenylcarbamate according to the IR and NMR spectra. The degree of polymerization as determined according to GPC was 200.

Elementary analysis: C, 60.93%; H, 4.68%; N, 7.93%; calculated for $(C_{27}H_{25}N_3O_8)_n$: C, 62.42%; H, 4.85%; N, 8.09%.

Synthesis Example 6

102 g of silica gel (Lichrospher SI 4000; a product of Merck & Co.) was dried at 180° C. for 2 h and then dispersed in a mixture of 600 ml of dry benzene, 6 ml of pyridine and 20 ml of 3-aminopropyltriethoxysilane to effect the reaction under reflux for 16 h. After the completion of the reaction, the reaction mixture was poured into 2 l of methanol and the modified silica gel was filtered.

0.76 g of the cellulose trisphenylcarbamate obtained in Synthesis Example 5 was dissolved in a solvent mixture of 10 ml of dioxane and 5 ml of ethanol. After removing a very small amount of an insoluble matter, 3.0 g of the modified silica gel was mixed with 5 ml of the solution and the solvent was distilled off under reduced pressure. This carrying process was repeated further twice to obtain cellulose trisphenylcarbamate-carrying silica gel.

Example 3

The carrying silica gel prepared in Synthesis Example 6 was packed in a stainless steel column having a length of 25 cm and an inner diameter of 0.46 cm by slurry process. The high-performance liquid chromatograph used was Trirotar-II (a product of Nihon Bunko Kogyo Co., Ltd.) and detector used as Uvidec-III and DIP-181 polarimeter. The solvents used were (1) hexane/2-propanol (mixing volume ratio: 90/10), (2) hexane/2-propanol (80:20), (3) hexane/2-propanol/diethylamine (80:20:0.001), (4) ethanol/water (50:50) and (5) ethanol/water (70:30). The flow rate was 0.5 ml/min and column temperature was 25° C. in all the cases.

The results of the resolution of various racemic compounds are shown in Tables 3-1 to 3-4 and those of the separation of achiral compounds are shown in Table 4.

Measurement of molecular weight

The molecular weight was determined by GPC method using a calibration curve of standard polystyrene. The GPC column used was Shodex A 80M and the solvent was tetrahydrofuran.

TABLE 3

Optical resolution with cellulose trisphenylcarbamate

| Racemic compound | Eluent[a] | $k'_1$ (optical rotatory power)[b] | α | $R_S$ |
|---|---|---|---|---|
| 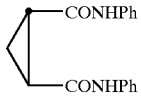 | 1 | 1.92 | 1.46 | 1.27 |
| 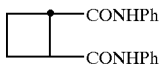 | 1 | 3.64 | 1.20 | — |
| 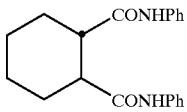 | 1 | 0.65 | 1.88 | 1.06 |
| 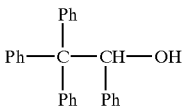 | 1 | 2.39 | 1.23 | 0.77 |
| 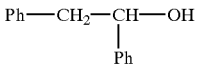 | 1 | 1.32 | 1.13 | 0.58 |

TABLE 3-continued

| Racemic compound | Eluent[a] | k'$_1$ (optical rotatory power)[b] | α | $R_S$ |
|---|---|---|---|---|
| | | Optical resolution with cellulose trisphenylcarbamate | | |
| 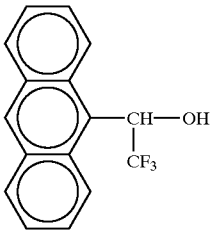 | 1 | 1.42 | 1.47 | 1.38 |
| 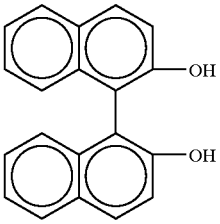 | 1 | 6.38 | 1.19 | 0.97 |
| 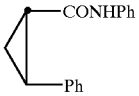 | 1 | 5.92 | 1.95 | 3.36 |
| 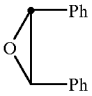 | 1 | 0.58(+) | 1.53 | 2.00 |
| 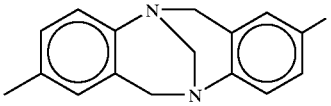 | 1 | 1.02 | 1.39 | 1.73 |
| 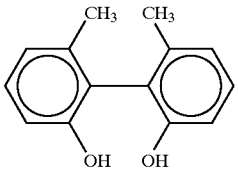 | 1 | 2.06(−) | 1.68 | 2.56 |
| 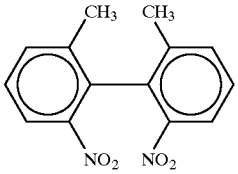 | 1 | 3.67(−) | 1.52 | 3.50 |
| $Cr(acac)_3$ | 1 | 2.00(−) | 1.48 | 1.14 |
| $Co(acac)_3$ | 1 | 2.24(+) | 1.31 | 0.75 |
| 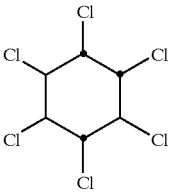 | 1 | 0.50(+) | 3.09 | 2.26 |

TABLE 3-continued

| Racemic compound | Eluent[a] | k'$_1$ (optical rotatory power)[b] | α | $R_S$ |
|---|---|---|---|---|
| | | Optical resolution with cellulose trisphenylcarbamate | | |
| 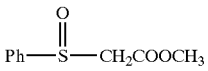 | 2 | 1.07(+) | 1.08 | 0.53 |
| 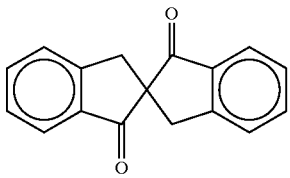 | 3 | 6.38(−) | 1.24 | 1.07 |
| 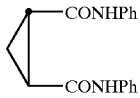 | 4 | 4.27(−) | 1.22 | 0.86 |
| 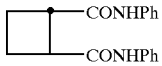 | 4 | 5.35(+) | 1.12 | — |
| 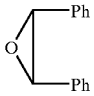 | 4 | 11.3(+) | 1.36 | 1.74 |
| 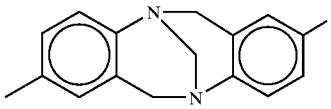 | 4 | 6.70(+) | 1.17 | 0.85 |
| 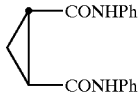 | 5 | 0.49(−) | 1.13 | — |
| 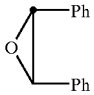 | 5 | 1.85(+) | 1.31 | 1.58 |
| 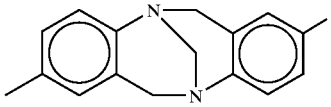 | 5 | 1.30(+) | 1.21 | 0.9 |
| 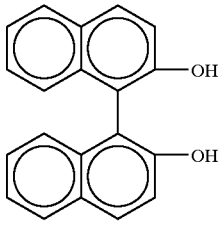 | 5 | 0.85(+) | 1.27 | 0.68 |

[a]eluent 1: hexanes/2-propanol (90/10)
eluent 2: hexanes/2-propanol (80/20)
eluent 3: hexanes/2-propanol/diethylamine (80:20:0.001)
eluent 4: ethanol/water(50:50)
eluent 5: ethanol/water(70:30)
[b]wavelength: 365 am

TABLE 4

Separation of achiral compounds with cellulose trisphenylcarbamate[a]

| Compound | Retention time (min) |
|---|---|
| 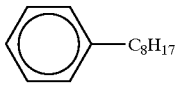 | 6.30 |
| 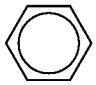 | 6.80 |
| 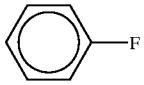 | 6.90 |
| 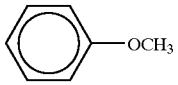 | 7.60 |
| 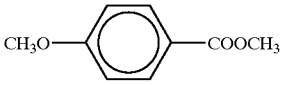 | 8.33 |
| 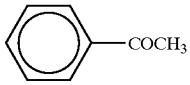 | 8.65 |
| 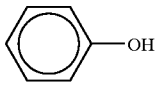 | 8.95 |
| 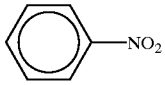 | 10.05 |
| 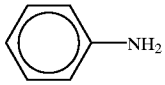 | 15.25 |
| 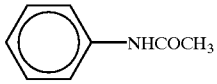 | 16.30 |
| $CH_3COOC_2H_5$ | 8.85 |
| $CH_3COCH_3$ | 9.75 |
| $Et_3N$ | 6.75 |
| $Et_3NH$ | 7.70 |

[a]eluent: hexane/2-propanol (80:20)

Synthesis Example 7

Cellulose triacetate having a number-average degree of polymerization of 110 and a degree of acetylation of 2.49 was dissolved in 1 l of acetic acid. 5.2 ml of water and 5 ml of conc. sulfuric acid were added to the resulting solution and the reaction was carried out at 80° C. for 3 h. The reaction liquid was cooled and sulfuric acid was neutralized with an excess amount of an aqueous magnesium acetate solution. The resulting solution was added to 3 l of water to precipitate cellulose triacetate having a reduced molecular weight. After filtration through a glass filter (G 3), it was dispersed in 1 l of water. After filtration followed by vacuum drying, the obtained product was dissolved in methylene chloride and then reprecipitated from 2-propanol. The dissolution and the reprecipitation were repeated twice to effect the purification. The product was dried. According to the IR and NMR spectra, the product was identified with cellulose triacetate. The number-average molecular weight of the product as determined by vapor pressure osmometry was 7900 which corresponded to the number-average degree of polymerization of 27. The vapor pressure osmometry was conducted with a vapor pressure osmometer Corona 117 using a solvent mixture of chloroform/1% ethanol.

10.0 g of the resulting low-molecular weight cellulose triacetate was dissolved in 100 ml of pyridine. 8.0 ml of 100% hydrazine hydrate was added to the solution. The mixture was left to stand at room temperature for 1 h and then heated to 90° to 100° C. A precipitate thus formed was filtered through a glass filter and washed with pyridine. According to the IR spectrum, the obtained product was identified with cellulose.

100 ml of dry pyridine was added to a mixture of 5 g of the resulting low molecular weight cellulose and a small amount of pyridine to obtain a dispersion. 100 ml of benzene was added to the dispersion to remove water. After distillation through a rectifier tube, the remaining suspension of the low molecular weight cellulose in pyridine was heated to 60° to 70° C. 16.3 ml of phenyl isocyanate was added dropwise to the suspension under stirring. The mixture was kept at 100° to 105° C. for 3 h 35 min. Pyridine and phenyl isocyanate were distilled off under reduced pressure and the reaction mixture was dissolved in methylene chloride. A by-product insoluble in methylene chloride was filtered out through a glass filter (G 3) and a soluble matter was fractionated with 2-propanol. The 2-propanol-insoluble product was obtained in an amount of 5.67 g as a light yellow solid. According to the IR and NMR spectra, the product was identified as cellulose trisphenylcarbamate.

IR spectrum: 3500 $cm^{-1}(\nu_{NH})$, $3300^{-1}cm(\nu_{NH})$, 1700 $cm^{-1}(\nu_{c=0})$, 1530 $cm^{-1}(\nu_{NH})$, NMR spectrum: 18 H Broad singlet centered at δ7 7 H multiplets δ6.0~3.0.

Synthesis Example 8

Silica gel (Lichrospher SI 1000, a product of Merck & Co.) was dried by heating to 120° to 150° C. in dry nitrogen stream for 2 to 10 h. 20 g of the dried silica gel was suspended in 100 ml of anhydrous benzene. 6 g of 3-aminopropyltrimethoxysilane was added thereto and the mixture was heated under reflux in dry nitrogen stream. While removing formed methanol from the reaction system, the reaction was carried out for 5 to 10 h. After the completion of the reaction, the reaction mixture was cooled to room temperature and filtered through a glass filter. The resulting modified silica gel was washed with anhydrous benzene and dried at 40° C. in vacuum.

6 g of the silica gel treated with the aminopropylsilane was dried at 80° C. under reduced pressure for 2 h and then dispersed in 50 ml of dry methylene chloride. 2 ml of triethylamine and 1 ml of phenyl isocyanate were added to the dispersion and mixed well. The mixture was left to stand for one day and then heated to 40° C. for 1 h. The solvent was removed by decantation and the residue was washed with methylene chloride, ethanol and acetone and dried.

0.9 g of cellulose trisphenylcarbamate obtained in Synthesis Example 7 was dissolved in 4.5 ml of methylene chloride. The resulting solution was mixed with 3.5 g of the modified silica gel. The solvent was distilled off under reduced pressure to obtain a cellulose trisphenylcarbamate-carrying silica gel.

Example 4

The silica gel carrying cellulose trisphenylcarbamate obtained in Synthesis Example 8 was packed in a stainless steel column having a length of 25 cm and an inner diameter of 0.46 cm by slurry method. The high-performance liquid chromatograph used was Trirotar-SR (a product of Nihon Bunko Kogyo Co., Ltd.) and the detector used was Uvidec-V. The flow rate was 0.2 ml/min and hexane/2-propanol (9:1) was used as the solvent. The results of resolution of various racemic compounds are shown in Table 5.

TABLE 5

Optical resolution of racemic compounds

| Racemic compound | Volume ratio $k'_1$ | Volume ratio $k'_2$ | Resolution factor $\alpha$ | Rate of separation Rs |
|---|---|---|---|---|
| 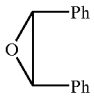 | 1.13 | 1.39 | 1.23 | 1.89 |
| 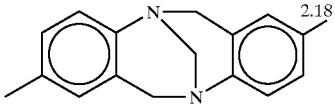 | 2.18 | 2.60 | 1.19 | 1.30 |
| 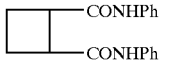 | 4.50 | 5.60 | 1.24 | 0.90 |
| 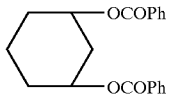 | 2.33 | 2.70 | 1.16 | 0.5 |
| 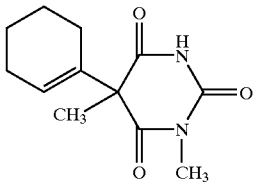 | 11.9 | 13.3 | 1.12 | — |

Synthesis Example 9

10 g of silica beads (Lichrospher SI 1000; a product of Merck & Co.) was placed in a 200 ml round-bottom flask with a side arm. After vacuum-drying in an oil bath at 120° C. for 3 h, $N_2$ was introduced therein. 100 ml of toluene which had been preliminarily distilled in the presence of $CaH_2$ was added to the silica beads. 3 ml of diphenyldimethoxysilane (KBM 202; a product of Shin'etsu Kagaku Co., Ltd.) was added to the mixture and they were stirred together and then reacted at 120° C. for 1 h. After distilling off 3 to 5 ml of toluene, the reaction was carried out at 120° C. for 2 h. The mixture was filtered through a glass filter, washed with 50 ml of toluene three times and then with 50 ml of methanol three times and dried in vacuum at 40° C. for 1 h.

About 10 g of the silica beads were placed in the 200 ml round-bottom flask with a side arm. After vacuum drying at 100° C. for 3 h, the pressure was returned to the atmospheric pressure and the mixture was cooled to room temperature. Then, $N_2$ was introduced therein. 100 ml of distilled toluene was added to the dried silica beads. 1 ml of N,O-bis (trimethylsilyl)acetamide (a trimethylsilylating agent) was added thereto and the mixture was stirred to effect the reaction at 115° C. for 3 h. The reaction mixture was filtered through a glass filter, washed with toluene and dried under vacuum for about 4 h.

Synthesis Example 10

Cellulose triacetate (a product of Daicel Ltd.) having a number-average degree of polymerization of 110 and a degree of substitution of 2.97 was dissolved in 1 l of acetic acid (a product of Kanto Kagaku Co.). 5.2 ml of water and 5 ml of conc. sulfuric acid were added to the resulting solution and the reaction was carried out at 80° C. for 3 h. The reaction mixture was cooled and sulfuric acid was neutralized with an excess amount of an aqueous magnesium acetate solution. The resulting solution was added to 3 l of water to precipitate cellulose triacetate having a reduced molecular weight. After filtration through a glass filter (G3), it was dispersed in 1 l of water. After filtration followed by vacuum drying, the obtained product was dissolved in methylene chloride and reprecipitated from 2-propanol. The dissolution and the reprecipitation were repeated twice to effect the purification. The product was dried. According to the IR and NMR spectra, the product was identified with cellulose triacetate. The number-average molecular weight of the product as determined by vapor pressure osmometry was 7900, which corresponded to the number-average degree of polymerization of 27. The vapor pressure osmometry was conducted with a vapor pressure osmometer Corona 117 using a solvent mixture of chloroform/1% ethanol.

60 g of the obtained cellulose triacetate was dispersed in 200 ml of 2-propanol. 60 ml of 100% hydrazine hydrate (a product of Nakai Kagaku Co.) was added dropwise slowly to the dispersion under gentle stirring. The suspension was maintained at 60° C. for 3 h and the resulting cellulose was filtered through a glass filter, washed with acetone repeatedly and vacuumdried at 60° C. In the IR spectrum of the product, no absorption band due to the carbonyl group at around 1720 $cm^{-1}$ was observed and the IR spectrum coincided with that of cellulose.

Synthesis Example 11

70 ml of dehydrated pyridine, 7.7 ml of dehydrated triethylamine and 50 mg of 4-dimethylaminopyridine were added to 1.5 g of the cellulose obtained in Synthesis Example 10. 12.2 g of thiophene-2-carbonyl chloride was added to the mixture under stirring. The mixture was stirred at 100° C. for 5 h to carry out the reaction. After cooling, the product was added to 400 ml of ethanol under stirring to form precipitates, which were filtered through a glass filter and then washed thoroughly with ethanol. After vacuum drying, the product was dissolved in 30 ml of methylene chloride. An insoluble matter was removed and the product was reprecipitated from 400 ml of ethanol. The precipitate was filtered and washed with ethanol. After removing the liquid, the product was dried.

Thus, 3.9 g of cellulose thiophene-2-carboxylate was obtained.

The product was dissolved in methylene chloride and the solution was applied on a sodium chloride tablet and dried. The infrared absorption spectrum of the product had the following characteristic absorption bands:

3100 $cm^{-1}$: stretching vibration of aroamtic C—H,

1720 $cm^{-1}$: stretching vibration of C═O of carboxylic acid ester 1360, 1420, 1520 $cm^{-1}$: stretching vibration of thiophene ring, 1260 $cm^{-1}$: stretching vibration of C—O of ester, 1060 to 1160 $cm^{-1}$: stretching vibration of C—O—C of cellulose, and 860 $cm^{-1}$: out-of-plane deformation vibration of disubstituted thiophene.

Substantially no absorption at around 3450 $cm^{-1}$ due to OH of cellulose was observed. This fact suggested that the product substantially comprised a trisubstituted compound. In the proton NMR spectrum determined in $CDCl_3$, the characteristic absorptions were as follows:

6.8 to 7.8 ppm: proton of thiophene ring, 2.8 to 5.4 ppm: protons of the cellulose ring and methylene in position 6.

The ratio of the thiophene ring proton to the cellulose proton was about 9:7, which coincided with that of the trisubstituted compound.

According to elementary analysis of the product, the sulfur content thereof was 19.40% which suggested that the product substantially comprised a trisubstituted compound.

Example 5

1.2 g of cellulose tris(thiophene-2-carboxylate) obtained in Synthesis Example 11 was dissolved in 7.5 ml of dichloromethane. The solution was filtered. The silica gel particles obtained in Synthesis Example 9 were impregnated with 7.5 ml of the resulting solution. The solvent was distilled off under reduced pressure to obtain powdery, supported material.

Application Example 1

The silica beads carrying cellulose tris(thiophene-2-carboxylate) obtained in Example 5 were packed in a stainless steel column having a length of 25 cm and an inner diameter of 0.46 cm by slurry process. The high-performance liquid chromatograph used was Trirostar-RS (a product of Nihon Bunko Kogyo Co., Ltd.) and the polarimeter detector was DIP-181 (a product of Nihon Bunko Kogyo Co., Ltd.). The results of the resolution of trans-stilbene oxide are shown in Table 6.

In the determination effected by using the polarimeter as the detector of the high-performance chromatograph, the terms were defined as follows:

$$I' = \frac{\left(\begin{array}{c}\text{time required for attaining the top}\\ \text{of the peak of antipode with the}\\ \text{polarimeter detector}\end{array}\right) - (\text{dead time})}{(\text{dead time})}$$

$$\beta = \frac{(I' \text{ of antipode adsorbed more strongly})}{(I' \text{ of antipode adsorbed less strongly})}$$

TABLE 6

| Racemic compound | $I_1'$ | $I_2'$ | β | Flow rate ml/min |
|---|---|---|---|---|
| 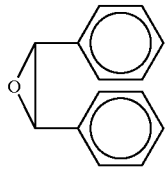 | 1.88 | 2.28 | 1.21 | 1.0 |

Solvent: hexane/2-propanol (9:1)

Synthesis Example 12

(Synthesis of Cellulose Tris-3-Chlorobenzoate)

3.0 g of cellulose obtained in Synthesis Example 10 and 0.05 g of 4-dimethylaminopyridine (a product of Aldrich Chemical Company) were suspended in a liquid mixture of 50 ml of pyridine and 15 ml of triethylamine. 25 g of m-chlorobenzoyl chloride (a product of Aldrich Chemical Company) was added to the suspension and the mixture was kept at 100° C. for 6 h. The reaction mixture was added to ethanol and the resulting precipitate was filtered, washed with ethanol repeatedly and vacuum-dried to obtain 9.1 g of a product. In the IR spectrum of the product, an absorption due to the ester bond (1740 $cm^{-1}$ and 1250 $cm^{-1}$) were remarkable but no absorption due to the O—H stretching vibration was recognized. This fact suggested that the product was a trisubstituted compound.

Synthesis Example 13

(Synthesis of Cellulose Tris-3,5-Dichlorobenzoate)

49.4 g of thionyl chloride and 0.21 g of pyridine were added to 20 g of 3,5-dichlorobenzoic acid and the mixture was refluxed for 20 hours. Excessive thionyl chloride was removed by distillation. Dry hexane was added to the residue and an insoluble matter was filtered out of the resulting solution and hexane was removed under reduced pressure. The remaining solution was crystallized. 3,5-Dichlorobenzoyl chloride was obtained quantitatively.

1.0 g of the cellulose obtained in Synthesis Example 10 was reacted with 11.6 g of 3,5-dichlorobenzoyl chloride in a mixture of 25 ml of pyridine, 4.3 ml of triethylamine and 50 mg of 4-dimethylaminopyridine at 100° C. for 5 h. The reaction mixture was added to ethanol and the precipitated cellulose tris-3,5-dichlorobenzoate was filtered, washed with ethanol and vacuum-dried. In the IR spectrum of the product, an absorption characteristic to the ester group was recognized but no absorption at around 3500 $cm^{-1}$ due to free hydroxy group was recognized. It was thus concluded that the product was a trisubstituted compound.

Synthesis Example 14

(Synthesis of Cellulose Tris-4-Chlorobenzoate)

2.43 g of the cellulose obtained in Synthesis Example 10 was reacted with 15.75 g of 4-chlorobenzoyl chloride in a mixture of 50 ml of pyridine, 20 ml of triethylamine and 200 mg of 4-dimethylaminophridine under stirring at 110° C. for 8 h. The product was added to 500 ml of methanol and the resulting precipitate was filtered, washed with water and then methanol and dissolved in benzene. The resulting solution was added to ethanol to purify the product by reprecipitation. The product was filtered and vacuum-dried. In the I.R. spectrum of the product, an absorption characteristic to the ester linkage was recognized but no absorption due to free hydroxyl group at around 3500 $cm^{-1}$ was recognized. It was thus considered that the product was a trisubstituted compound.

Example 6

1.2 g of cellulose tris(3-chlorobenzoate) obtained in Synthesis Example 12 was dissolved in 7.5 ml of dichloromethane. The silica beads obtained in Synthesis Example 9 were impregnated with 7.5 ml of the resulting solution. The solvent was removed under reduced pressure to obtain a powdery, supported material.

EXAMPLE 7

1.2 g of cellulose tris(3,5-dichlorobenzoate) obtained in Synthesis Example 13 was dissolved in 7.5 ml of dichloromethane. 3.2 g of silica beads obtained in Synthesis Example 9 were impregnated with 7.5 ml of the resulting solution. The solvent was removed under reduced pressure to obtain a powdery, supported material.

Example 8

Cellulose tris(4-chlorobenzoate) obtained in Synthesis Example 14 was supported on silica beads in the same manner as in Example 7 to obtain a powdery material.

Application Example 2

The silica beads carrying cellulose tris(3-chlorobenzoate) obtained in Example 6 were packed in a stainless steel column having a length of 25 cm and an inner diameter of 0.46 cm by a slurry process. The high-performance liquid chromatograph used was Trirotar-SR (a product of Nihon Bunko Kogyo Co., Ltd.) and the detector was UVIDEC-V. Various racemic compounds were resolved to obtain the results shown in Table 7.

TABLE 7

| Racemic compound | Volume ratio $k_1'$ | Volume ratio $k_2'$ | Resolution factor (α) | Rate of separation (Rs) | Flow rate (ml/min) |
|---|---|---|---|---|---|
| 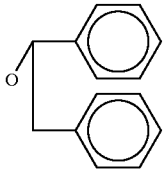 | 1.48 | 1.96 | 1.33 | 1.24 | 0.5 |
| 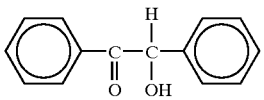 | 5.97 | 7.50 | 1.26 | 1.05 | 0.5 |
| 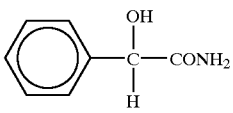 | 4.8 | 5.14 | 1.07 | — | 0.5 |

TABLE 7-continued

| Racemic compound | Volume ratio $k_1'$ | Volume ratio $k_2'$ | Resolution factor (α) | Rate of separation (Rs) | Flow rate (ml/min) |
|---|---|---|---|---|---|
| 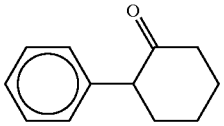 | 10.9 | 12.0 | 1.10 | — | 0.5 |

Solvent: hexane/2-propanol (9:1)

Application Example 3

The silica beads carrying cellulose tris(3,5-dichlorobenzoate) obtained in Example 7 were packed in a stainless steel column having a length of 25 cm and an inner diameter of 0.46 cm by a slurry process. The high-performance liquid chromatograph used was Trirotar-SR (a product of Nihon Bunko Kogyo Co., Ltd.) and the detector was Uvidec-V. Various racemic compounds were resolved to obtain the results shown in Table 8.

TABLE 8

| Racemic compound | Volume ratio $k_1'$ | Volume ratio $k_2'$ | Resolution factor (α) | Rate of separation (Rs) | Flow rate (ml/min) |
|---|---|---|---|---|---|
| 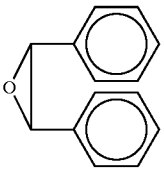 | 1.91 | 2.31 | 1.21 | 1.22 | 0.5 |
| 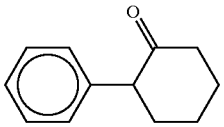 | 5.36 | 7.16 | 1.33 | 1.71 | 0.5 |
| 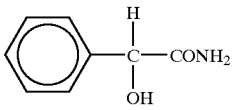 | 2.84 | 3.96 | 1.39 | 1.33 | 0.5 |
| 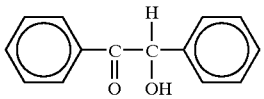 | 5.99 | 7.37 | 1.23 | 1.54 | 0.5 |

Solvent: hexane/2-propanol (9:1)

Application Example 4

The silica beads carrying cellulose tris(4-chlorobenzoate) obtained in Example 8 were packed in a stainless steel column having a length of 25 cm and an inner diameter of 0.46 cm by a slurry process. The high-performance liquid chromatograph used was Trirotar-SR (a product of Nihon Bunko Kogyo Co., Ltd.) and the detector was Uvidec-V. Various racemic compounds were resolved to obtain the results shown in Table 9.

TABLE 9

| Racemic compound | Volume ratio $k_1'$ | Volume ratio $k_2'$ | Resolution factor (α) | Rate of separation (Rs) | Flow rate (ml/min) |
|---|---|---|---|---|---|
| 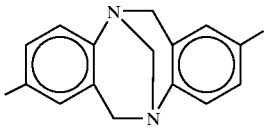 | 1.69 | 2.11 | 1.25 | 0.6 | 0.5 |
| 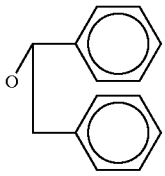 | 1.61 | 2.03 | 1.27 | 0.6 | 0.5 |

Solvent: hexane/2-propanol (9:1)

Synthesis Example 15

70 ml of dry pyridine, 7.7 ml of dry triethylamine and 50 mg of 4-dimethylaminopyridine were added to 1.5 g of the cellulose obtained in Synthesis Example 10. 12.9 g of phenylacetyl chloride was added to the mixture under stirring and the reaction was carried out at 100° C. for 5 h. After cooling, the product was added to 400 ml of ethanol under stirring to form a precipitate, which was filtered through a glass filter and washed thoroughly with ethanol. After drying in vacuum, the product was dissolved in 30 ml of methylene chloride to remove an insoluble matter and reprecipitated with 400 ml of ethanol. The precipitate was filtered and washed with ethanol. After dehydration followed by drying, 4.3 g of cellulose phenylacetate was obtained.

The product was dissolved in methylene chloride and the solution was applied on a plate of common salt and dried. The I.R. absorption spectrum of the product had the following characteristic absorption bands:

3050 $cm^{-1}$: C—H stretching vibration of the aromatic ring

1750 $cm^{-1}$: C═O stretching vibration of the carboxylic ester group

1610 $cm^{-1}$, 1500 $cm^{-1}$, 1460 $cm^{-1}$: skeletal vibration due to the C—C stretching of the benzene ring carbon atoms 1250 $cm^{-1}$: C—O stretching vibration of the ester group 1030~1160 $cm^{-1}$: C—O—C stretching vibration of cellulose 690~900 $cm^{-1}$: out-of-plane deformation vibration of the benzene ring Substantially no absorption due to OH of the cellulose at around 3450 $cm^{-1}$ was recognized. The product was substantially a trisubstituted compound. Its proton NMR spectrum in $CDCl_3$ had the following characteristic resonances:

6.0 to 7.8 ppm: proton of the benzene ring 3 to 4 ppm: methylene proton of the phenylacetyl acid group 3 to 5.4 ppm: protons of the cellulose ring and methylene on position 6.

Example 9

1.2 g of the product obtained in Synthesis Example 15 was dissolved in 7.5 ml of dichloromethane. The silica gel beads obtained in Synthesis Example 9 were impregnated with 7.5 ml of the resulting solution. The solvent was distilled off under reduced pressure to obtain a powdery, supported material.

Application Example 5

The silica beads carrying cellulose trisphenylacetate obtained in Example 9 were packed in a stainless steel column having a length of 25 cm and an inner diameter of 0.46 cm by a slurry process. The high-performance liquid chromatograph used was Trirotar-RS (a product of Nihon Bunko Koguo Co., Ltd.) and the detector was Uvidec-V.

Tr/öger's base was resolved to obtain the results shown in Table 10.

TABLE 10

Optical resolution of various racemic compounds

| Racemic compound | Volume ratio $k'_1$ | Volume ratio $k'_2$ | Resolution factor α | Flow rate ml/min |
|---|---|---|---|---|
| 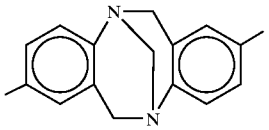 | 1.46 | 1.59 | 1.09 | 0.5 |

Solvent: hexane/2-propanol (9:1)

The embodiments of the invention in which an exclusive property or privilege is claimed are defined as follows:

[1. A separating agent which comprises a cellulose derivative selected from the group consisting of cellulose tribenzoate and cellulose tribenzoate ring-substituted with alkyl, alkenyl, alkynyl, nitro, halogen, amino, alkyl-substituted amino, cyano, hydroxyl, alkoxy, acyl, thiol, sulfonyl, carboxyl or alkoxy carbonyl, said cellulose derivative being supported on a porous carrier having a particle size of from 1 micron to 10 millimeters and a pore size of from 10 Angstrom units to 100 microns.]

[2. A separating agent as claimed in claim 1 in which said cellulose derivative is cellulose tribenzoate.]

[3. A separating agent as claimed in claim 1, wherein the amount of said cellulose derivative supported on said carrier is from 1–100 wt.% based on the weight of the carrier.]

[4. A separating agent as claimed in claim 1, wherein the ratio of pore size to particle size of said carrier is not larger than 0.1:1.]

[5. A separating agent as claimed in claim 1, wherein said carrier is an inorganic substance selected from the group consisting of silica, alumina, magnesia, titanium oxide, glass, silicate and kaolin.]

[6. A separating agent as claimed in claim 1, wherein said carrier is an organic substance selected from the group consisting of polystyrene, polyacrylamide and polyacrylate.]

[7. A separating agent as claimed in claim 1 in which said cellulose derivative is coated on said carrier and has been prepared by mixing said carrier with a solution of said cellulose derivative in a solvent therefor, and then removing said solvent.]

[8. A separating agent as claimed in claim 1, in which said carrier is an inorganic substance.]

[9. A separating agent as claimed in claim 8, in which said inorganic substance is silica gel.]

[10. A chromatographic isomer separating agent comprising a derivative of cellulose selected from the group consisting of cellulose tribenzoate and cellulose tribenzoate ring-substituted with alkyl, alkenyl, alkynyl, nitro, halogen, amino, alkyl-substituted amino, cyano, hydroxyl, alkoxy, acyl, thiol, sulfonyl, carboxyl or alkoxy carbonyl having a number average degree of polymerization in the range of 5–5000 supported on a solid carrier having a particle size of from 1 micron to 10 millimeters.]

[11. A chromagraphic isomer separating agent as claimed in claim 10 in which said cellulose derivative is cellulose tribenzoate.]

[12. A chromagraphic isomer separating agent as claimed in claim 10 in which said cellulose derivative is cellulose tris(3-chlorobenzoate).]

[13. A chromagraphic isomer separating agent as claimed in claim 10 in which said cellulose derivative is cellulose tris(3,5-dichlorobenzoate).]

[14. A chromagraphic isomer separating agent as claimed in claim 10 in which said cellulose derivative is cellulose tris(4-chlorobenzoate).]

[15. A chromatographic isomer separating agent as claimed in claim 10, wherein said cellulose derivative is immobilized on solid carrier particles, wherein said carrier particles are from 1 μm–10 mm in diameter and the amount of said cellulose derivative supported is from 1–100 wt.% based on the weight of the carrier particles.]

[16. A chromatographic isomer separating agent as claimed in claim 15 wherein said carrier particles are porous and have pore diameters of from 10 Å–100 μm.]

[17. A chromatographic isomer separating agent as claimed in claim 16, wherein said carrier particles have an approximate pore size to particle size ratio of no greater than 0.1:1.]

[18. A chromatographic isomer separating agent as claimed in claim 15, wherein said carrier is an inorganic substance selected from among silica, alumina, magnesia, titanium oxide, glass, silicate and kaolin.]

[19. A chromatographic isomer separating agent as claimed in claim 15, wherein said carrier is silica gel.]

[20. A chromatographic isomer separating agent as claimed in claim 15, wherein said carrier is an organic substance selected from the group consisting of polystyrene, polyacrylamide and polyacrylate.]

*21. In a chromatographic column used in the chiral separation of a chemical substance from a mixture containing the same, the improvement comprising said column containing a porous carrier having a pore size of 50 to 50,000 Å and supported thereon a cellulose derivative separating agent consisting of cellulose having a ring-substituted or unsubstituted phenyl group attached thereto through a urethane group, the separating agent being in a dissolved state during the supporting thereof on the carrier.*

*22. The column of claim 21, wherein said carrier has a particle size of about 1 μm to about 10 mm.*

*23. The column of claim 21, wherein said separating agent is cellulose trisphenylcarbamate.*

*24. The column of claim 21, wherein said phenyl group is ring-substituted with a group selected from among an alkyl group and a halogen group.*

*25. The column of claim 24, wherein said phenyl group is ring-substituted with an alkyl group.*

*26. The column of claim 24, wherein said phenyl group is ring-substituted with a halogen group.*

*27. The column of claim 26, wherein said halogen group is chloro.*

*28. The column of claim 21, wherein said porous carrier is silica.*

* * * * *